United States Patent [19]
Feingold et al.

[11] Patent Number: 6,056,757
[45] Date of Patent: May 2, 2000

[54] IMPLANTATION DEVICE WITH DEFORMABLE NOZZLE TIP FOR IMPLANTING A DEFORMABLE INTRAOCULAR LENS

[75] Inventors: Vladimir Feingold, Laguna Niguel; Daniel C. Eagles, Capistrano Beach, both of Calif.

[73] Assignee: STAAR Surgical Company, Inc., Monrovia, Calif.

[21] Appl. No.: 08/808,576

[22] Filed: Feb. 28, 1997

Related U.S. Application Data

[63] Continuation-in-part of application No. 08/649,433, May 17, 1996, which is a continuation-in-part of application No. 08/570,564, Dec. 11, 1995, which is a continuation-in-part of application No. 08/547,908, Oct. 25, 1995, which is a continuation-in-part of application No. 08/547,295, Oct. 25, 1995, which is a continuation-in-part of application No. 08/449,103, May 24, 1995, which is a continuation-in-part of application No. 08/197,604, Feb. 17, 1994, which is a continuation-in-part of application No. 08/403,530, Mar. 14, 1995, which is a continuation-in-part of application No. 08/221,013, Apr. 1, 1994, which is a continuation-in-part of application No. 08/401,523, Mar. 10, 1995, which is a continuation-in-part of application No. 08/368,792, Jan. 4, 1995, which is a continuation-in-part of application No. 08/345,360, Nov. 18, 1994, which is a continuation-in-part of application No. 08/240,520, Jul. 19, 1994, which is a continuation-in-part of application No. 08/220,999, Apr. 1, 1994, which is a continuation-in-part of application No. 08/196,855, Feb. 15, 1994, which is a continuation-in-part of application No. 08/195,717, Feb. 14, 1994, which is a continuation-in-part of application No. 07/953,251, Sep. 30, 1992, abandoned.

[51] Int. Cl.$^7$ .................................................. A61F 9/00
[52] U.S. Cl. .............................................. 606/107; 623/6
[58] Field of Search .................................. 606/107, 166; 623/4, 6; 604/19, 57, 59

[56] References Cited

U.S. PATENT DOCUMENTS 5,474,562  12/1995  Orchowski et al. ..................... 606/107
5,653,715   8/1997  Reich et al. ............................ 606/107

*Primary Examiner*—Glenn K. Dawson
*Attorney, Agent, or Firm*—Klima & Pezzlo, P.C.

[57] ABSTRACT

A deformable intraocular lens implanting device for implanting a deformable intraocular lens into the eye. The device includes a deformable nozzle tip portion having a wall portion defining a nozzle tip lens delivery passageway portion, the wall portion having a deformable transverse cross-sectional profile which deforms as an intraocular lens is advanced through the nozzle tip lens delivery passageway portion.

10 Claims, 11 Drawing Sheets

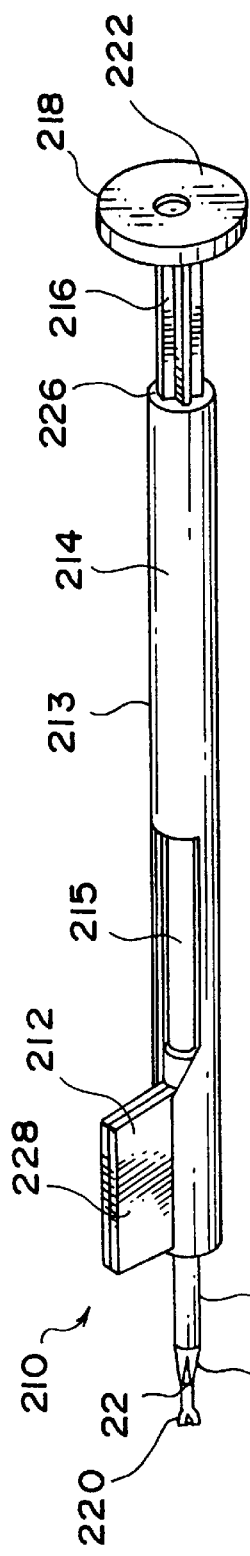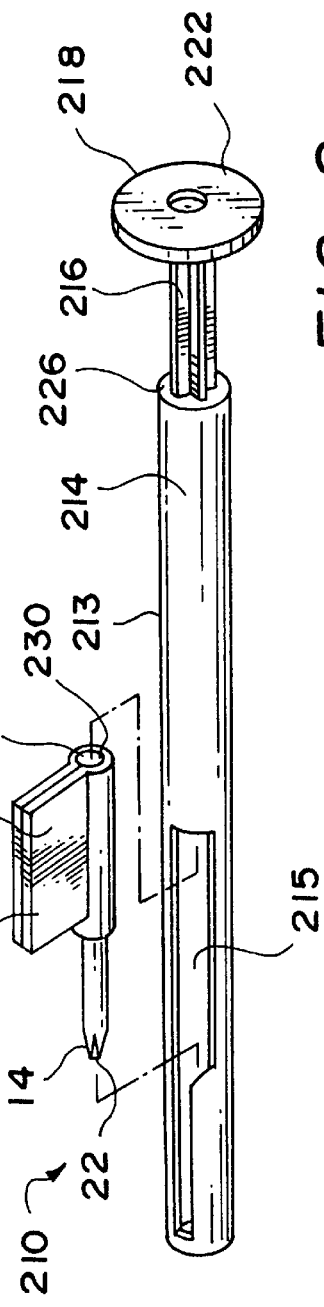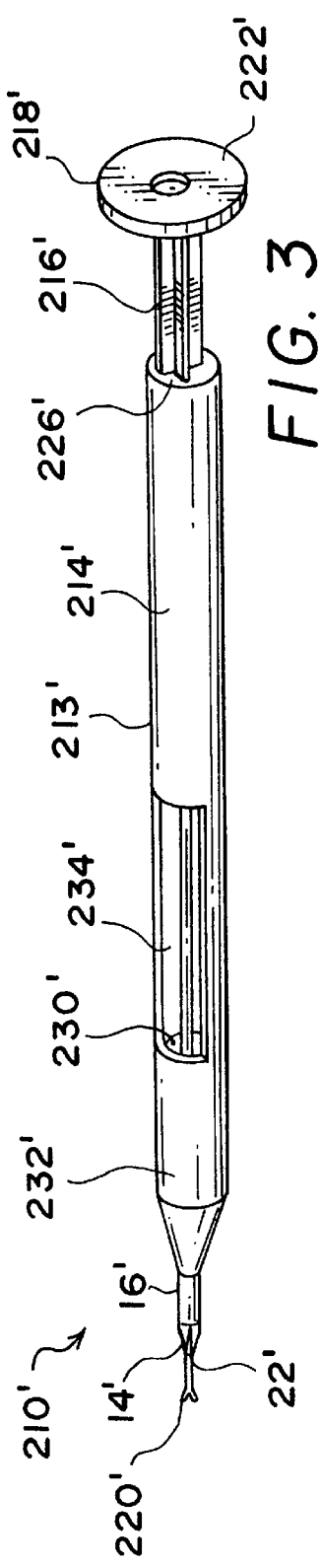

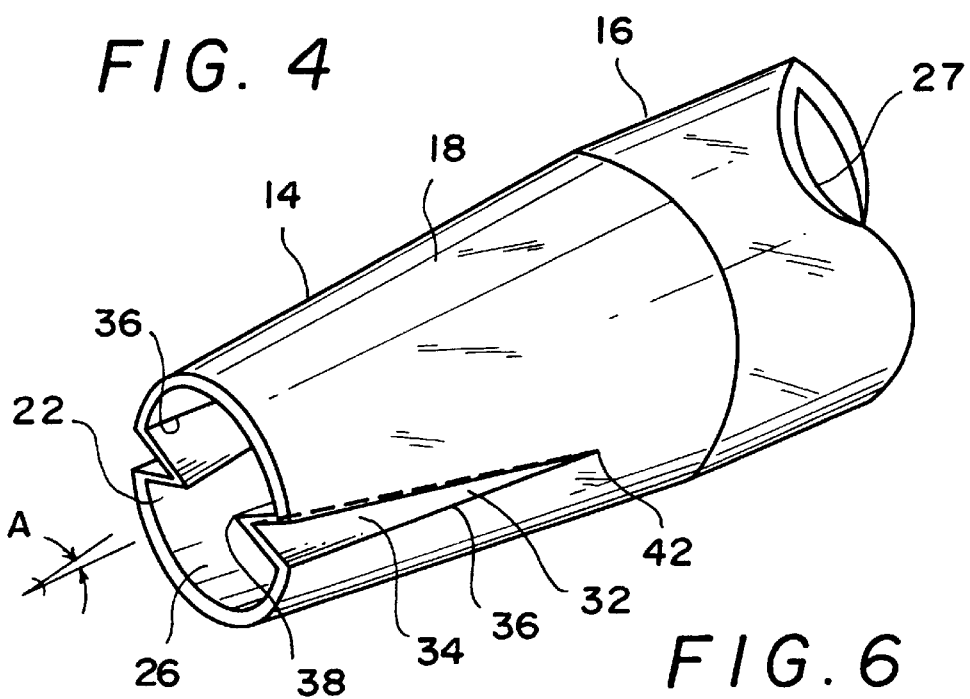
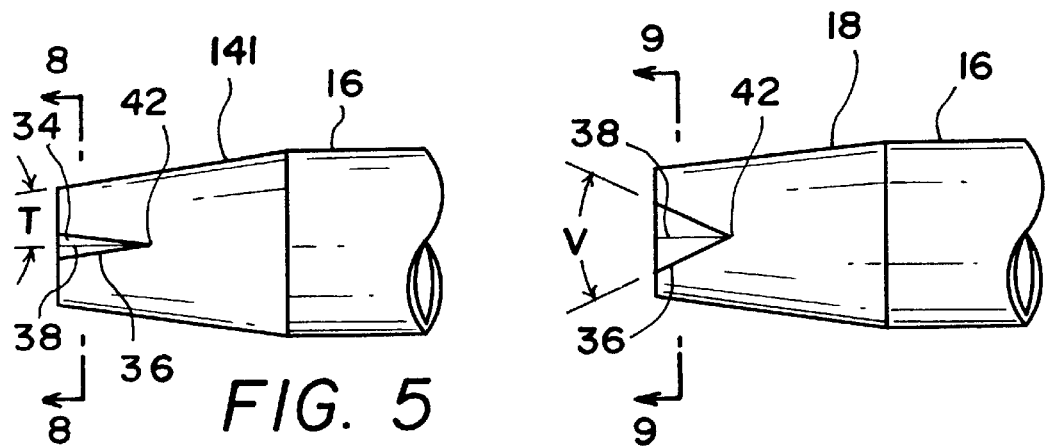
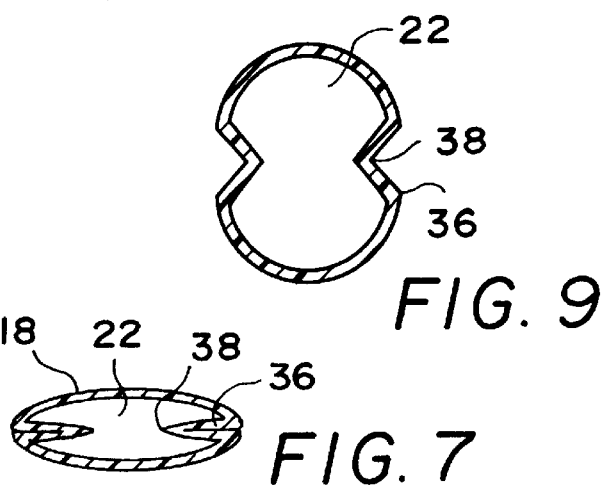

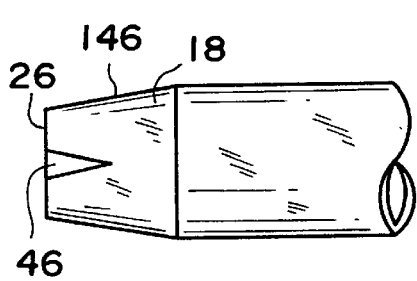
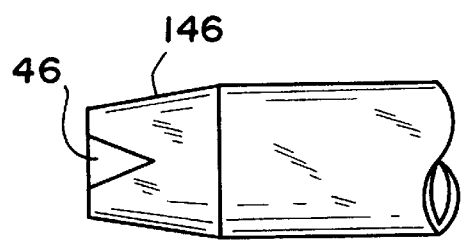
FIG. 31  FIG. 32
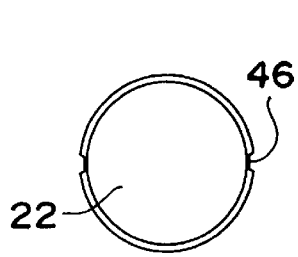
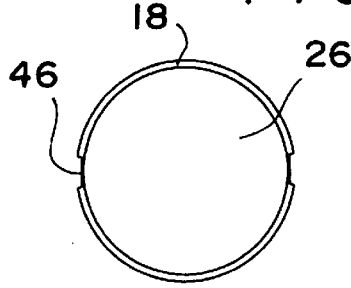
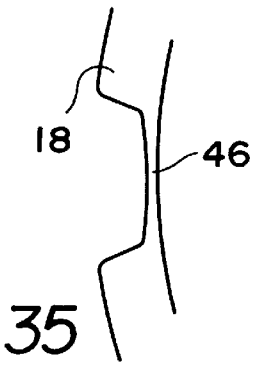
FIG. 33  FIG. 34  FIG.35
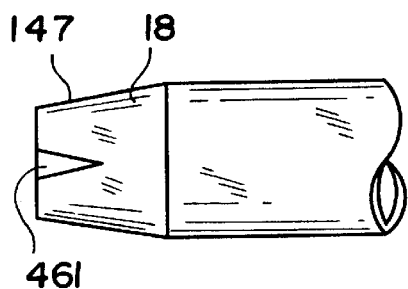
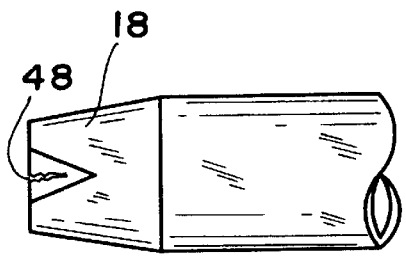
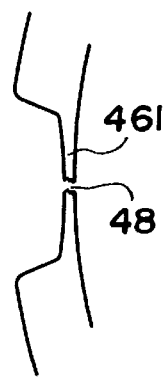
FIG. 36  FIG. 37
FIG. 38
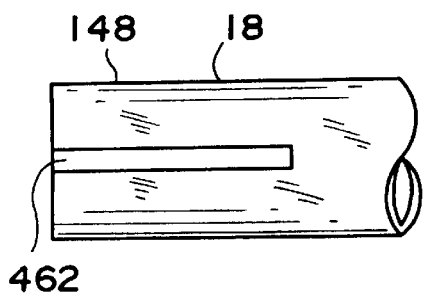
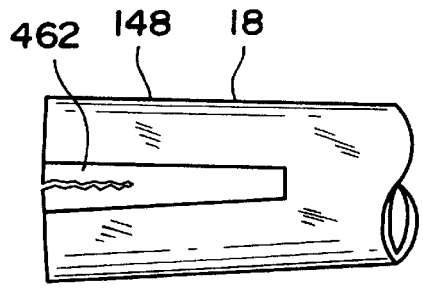
FIG. 39  FIG. 40

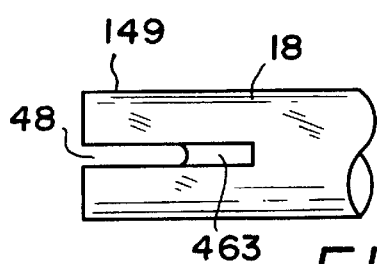
FIG. 41
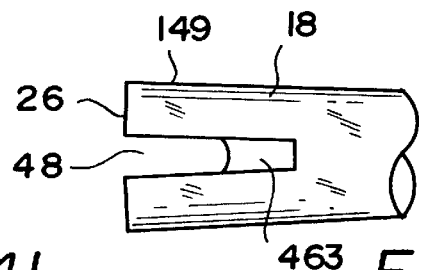
FIG. 42
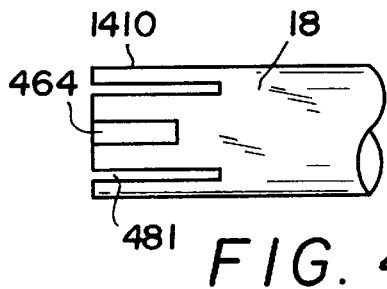
FIG. 43
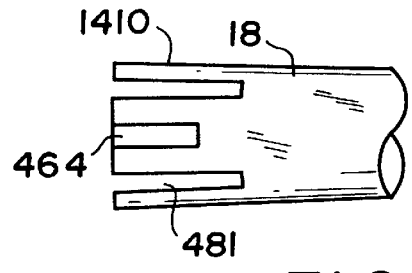
FIG. 44
FIG. 45
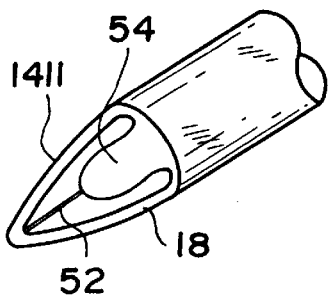
FIG. 48
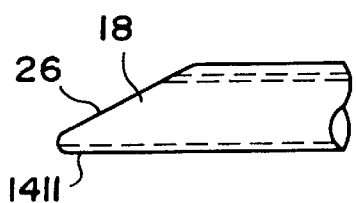
FIG. 46
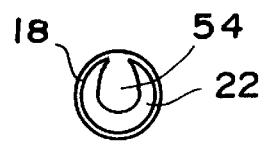
FIG. 47
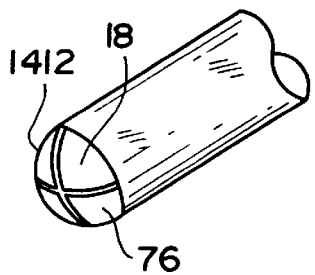
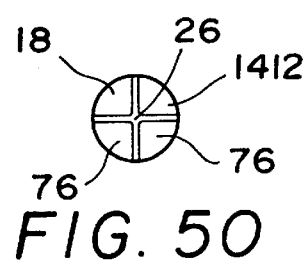
FIG. 49    FIG. 50
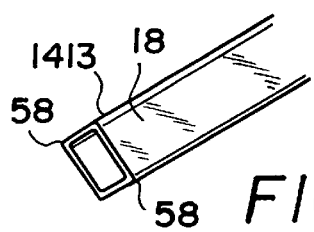
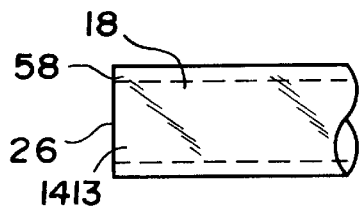
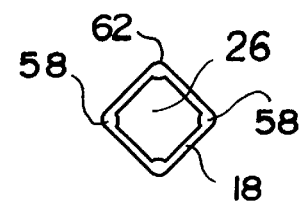
FIG. 51    FIG. 52    FIG. 53

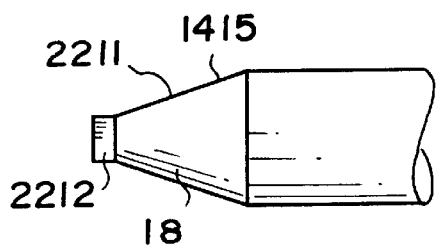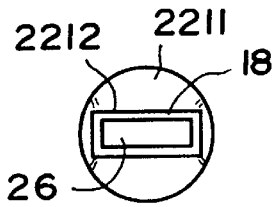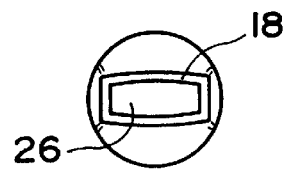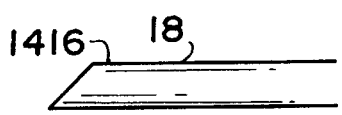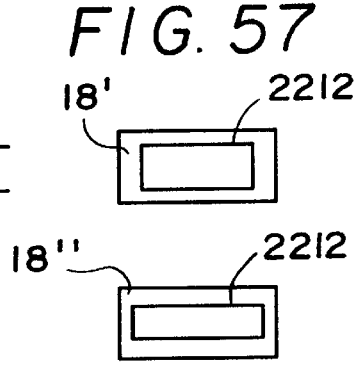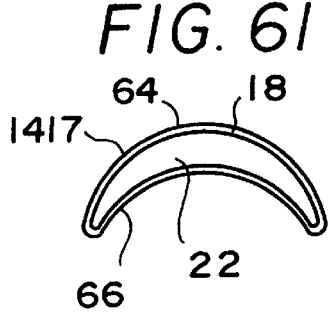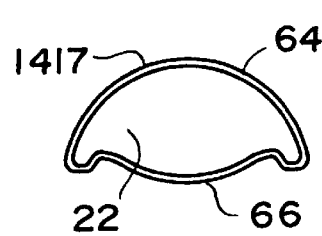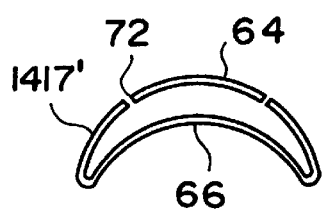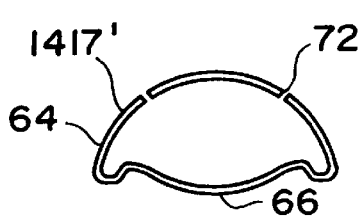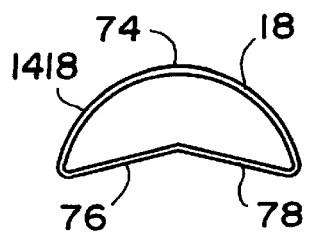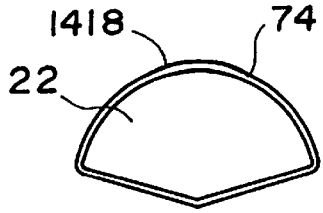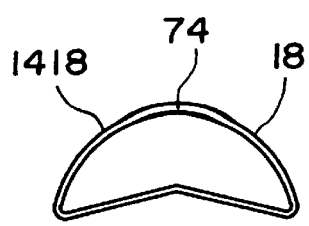

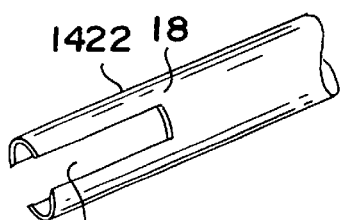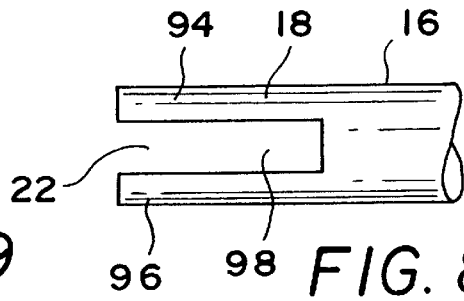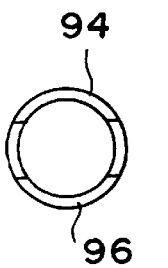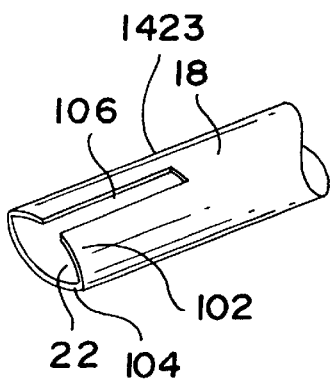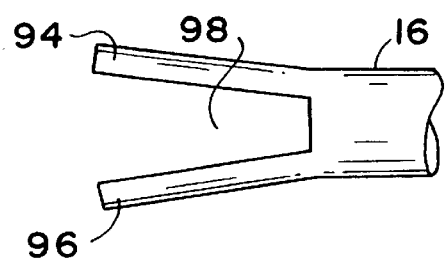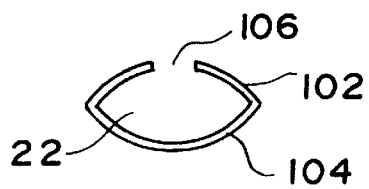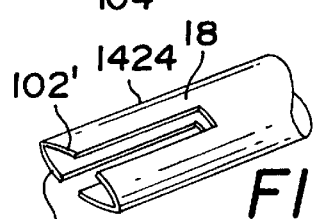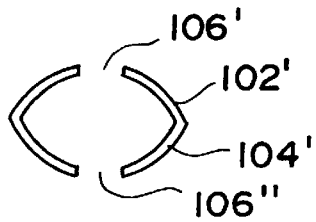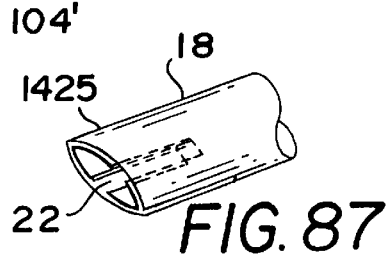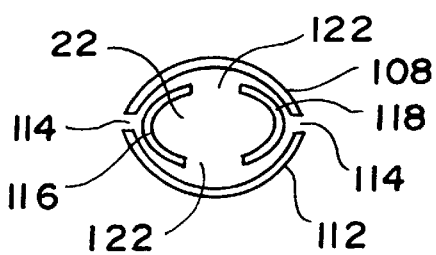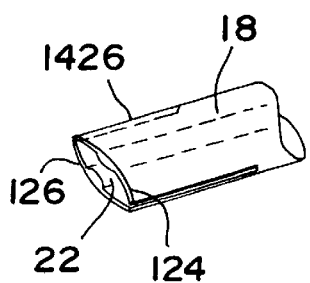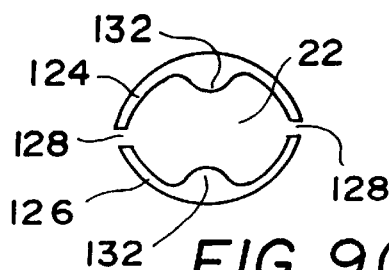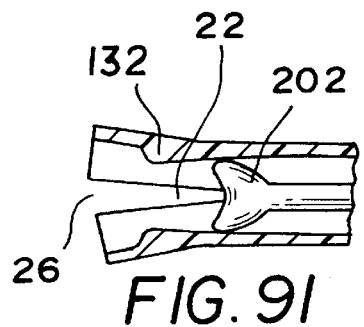

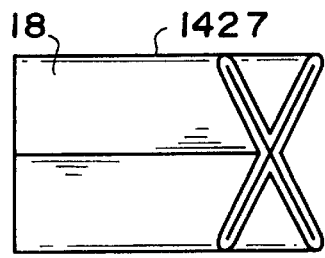
FIG. 92
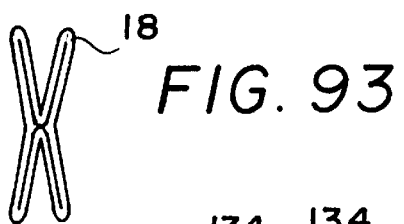
FIG. 93
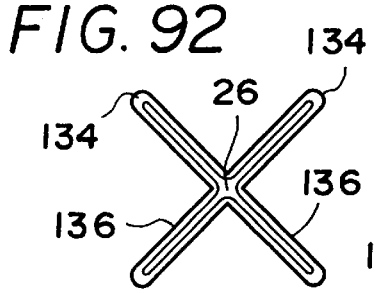
FIG. 94
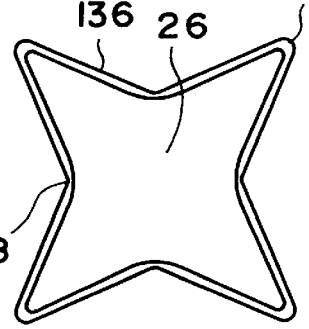
FIG. 95
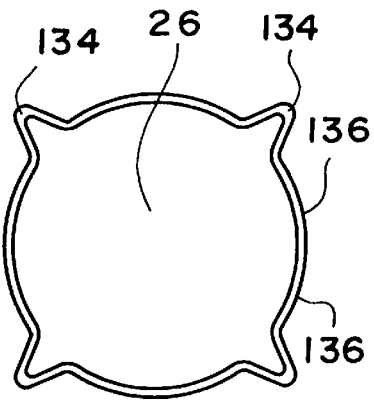
FIG. 96
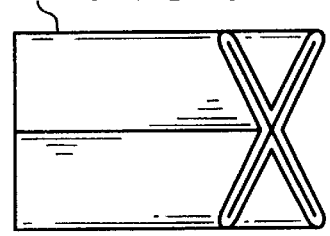
FIG. 97
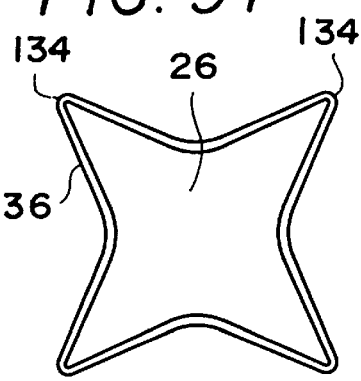
FIG. 99
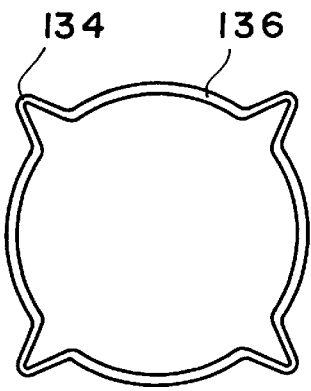
FIG. 100
FIG. 98
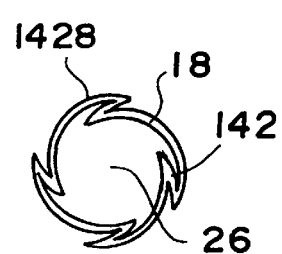
FIG. 101
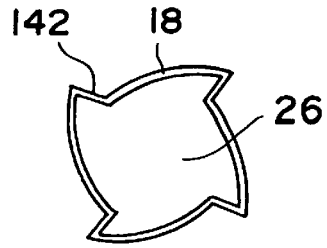
FIG. 102
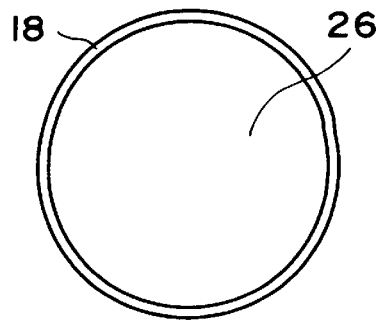
FIG. 103

IMPLANTATION DEVICE WITH DEFORMABLE NOZZLE TIP FOR IMPLANTING A DEFORMABLE INTRAOCULAR LENS

RELATED APPLICATIONS

This is a Continuation-In-Part (CIP) of:

1) U.S. patent application entitled "Apparatus and Method for Preparing an Intraocular Lens for Insertion", Ser. No. 08/649,433, filed May 17, 1996;
2) U.S. patent application entitled "Deformable Intraocular Lens Injecting Apparatus with Deformable Tip Plunger", Ser. No. 08/570,564, filed Dec. 11, 1995;
3) U.S. patent application entitled "Transverse Hinged Deformable Intraocular Lens Injecting Apparatus", Ser. No. 08/547,908, filed Oct. 25, 1995;
4) U.S. patent application entitled "Transverse Hinged Deformable Intraocular Lens Injecting Apparatus, Ser. No. 08/547,295, filed Oct. 25, 1995;
5) U.S. patent application entitled "Deformable Intraocular Lens Injection System, and Method Thereof", Ser. No. 08/449,103, filed May 24, 1995; which is a CIP of 08/197,604 filed Feb. 17, 1994;
6) U.S. patent application entitled "Deformable Intraocular Lens Injecting Device, Ser. No. 08/403,530, filed Mar. 14, 1995; which is a CIP of 08/221,013 filed Apr. 1, 1994;
7) U.S. patent application entitled "Deformable Intraocular Lens Insertion System", Ser. No. 08/401,523, filed Mar. 10, 1995;
8) U.S. patent application entitled "Deformable Intraocular Lens Injection Systems and Methods of Use Thereof", Ser. No. 08/368,792, filed Jan. 4, 1995;
9) U.S. patent application entitled "Disposable Intraocular Lens Insertion System, Ser. No. 08/345,360, filed Nov. 18, 1994;
10) U.S. patent application entitled "Intraocular Lens Insertion System", Ser. No. 08/240,520, filed Jul. 19, 1994;
11) U.S. patent application entitled "Method for the Surgical Implantation of a Deformable Intraocular Lens in the Eye", Ser. No. 08/220,999, filed Apr. 1, 1994;
12) U.S. patent application entitled "Hingeless Cartridge for Insertion of a Deformable Intraocular Lens", Ser. No. 08/196,355, filed Feb. 15, 1994;
13) U.S. patent application entitled "Methods of Implantation of a Deformable Intraocular Lens, Ser. No. 08/195,717, filed Feb. 14, 1994; and
14) U.S. patent application entitled "Intraocular Lens Insertion System", Ser. No. 07/953,251, filed Sep. 30, 1992, now abandoned, all fully incorporated herein by reference.

FIELD OF THE INVENTION

This invention relates to an improved nozzle tip for use with a surgical device in the implantation of deformable intraocular lenses into the eye.

BACKGROUND OF THE INVENTION

The size of the incision in the ocular tissue necessary to implant an intraocular lens within the capsule of the eye continues to decrease with the progress of intraocular lens deformation technology. One downside of this progress is that increasingly high stresses are being created in the material of the intraocular lens during the implantation procedure. Since deformable intraocular lenses are typically made of materials having elastic properties, increased lens deformation is opposed by a proportionally strong tendency of the lens to return from a deformed configuration, that is, to release the stresses associated with deformation. While these stresses must be relieved for proper implantation, complications may arise if the lens is simply allowed to "spring" back from a deformed configuration within the eye, for example, the eye may be injured, the lens may be damaged or the lens may be improperly oriented within the eye. Thus, a new problem has arisen in the art of intraocular lens implantation procedure: controlling the release of a deformed intraocular lens into the capsule of the eye. The present invention solves this problem.

SUMMARY OF THE INVENTION

A first object of the present invention is to provide an improved nozzle tip for a deformable intraocular lens implanting device for implanting a deformable intraocular lens into the eye.

A second object of the present invention is to provide a deformable nozzle tip which effects a controlled release of a deformed intraocular lens into the eye.

A third object of the present invention is to provide a deformable nozzle tip which will facilitate precise placement of the nozzle tip at the incision of the ocular tissue.

A fourth object of the present invention is to provide a deformable nozzle tip which will pass through ocular tissue easily and without damaging the ocular tissue.

A fifth object of the present invention is to provide a deformable nozzle tip which deforms to allow an intraocular lens to partially or fully return from a deformed configuration before the lens is ejected therefrom.

A sixth object of the present invention is to provide a deformable nozzle tip which will substantially return from a deformed configuration upon ejection of the intraocular lens therefrom into the capsule of the eye for easy removal of the nozzle tip from the eye.

A seventh object of the present invention is to provide a deformable nozzle tip which will not accelerate a lens into the capsule of the eye.

An eighth object of the present invention is to provide a deformable intraocular lens implanting device for implanting a deformable intraocular lens into the eye, the device including a holder having a receiver, a plunger movably disposed relative to said holder, said plunger having a plunger tip, a microcartridge disposed within said receiver, said microcartridge including a lens receiving portion, and a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion.

BRIEF DESCRIPTION OF THE DRAWINGS

FIG. 1 is a side elevational view of a preferred embodiment of a deformable intraocular lens implantation device including a deformable nozzle tip according to the present invention.

FIG. 2 is an exploded side elevational view of the lens implantation device shown in FIG. 1.

FIG. 3 is a side elevational view of an alternative embodiment of a deformable intraocular lens implantation device including a deformable nozzle tip according to the present invention.

FIG. 4 is a perspective view of the deformable nozzle tip shown in FIGS. 1–3.

FIG. 5 is a side elevational view of the deformable nozzle tip shown in FIG. 4.

FIG. 6 is a side elevational view of the deformable nozzle tip shown in FIG. 4 in a substantially deformed configuration.

FIG. 7 is a transverse cross-sectional view of the deformable nozzle tip shown in FIG. 5 in a substantially compressed state.

FIG. 8 is a cross-sectional view of the nozzle tip shown in FIG. 4 along the line 7—7.

FIG. 9 is a cross-sectional view of the nozzle tip shown in FIG. 4 in a substantially deformed configuration along the line 8—8.

FIG. 31 is a side elevational view of a eighth embodiment of a deformable nozzle tip according to the present invention.

FIG. 32 is a side elevational view of the nozzle tip shown in FIG. 31 in a substantially deformed configuration.

FIG. 33 is a distal end view of the deformable nozzle tip shown in FIG. 31 in a non-deformed configuration.

FIG. 34 is a distal end view of the deformable nozzle tip shown in FIG. 31 in a substantially deformed configuration.

FIG. 35 is a partial distal end view of the deformable nozzle tip shown in FIG. 31.

FIG. 36 is a side elevational view of an ninth embodiment of a deformable nozzle tip according to the present invention.

FIG. 37 is a side elevational view of the nozzle tip shown in FIG. 36 in a substantially deformed configuration.

FIG. 38 is a partial distal end view of the deformable nozzle tip shown in FIG. 36.

FIG. 39 is a side elevational view of a tenth embodiment of a deformable nozzle tip according to the present invention.

FIG. 40 is a side elevational view of the nozzle tip shown in FIG. 39 in a substantially deformed configuration.

FIG. 41 is a side elevational view of an eleventh embodiment of a deformable nozzle tip according to the present invention.

FIG. 42 is a side elevational view of the nozzle tip shown in FIG. 41 in a substantially deformed configuration.

FIG. 43 is a side elevational view of an twelfth embodiment of a deformable nozzle tip according to the present invention.

FIG. 44 is a side elevational view of the nozzle tip shown in FIG. 43 in a substantially deformed configuration.

FIG. 45 is a perspective view of a twelfth embodiment of a deformable nozzle tip according to the present invention.

FIG. 46 is a side elevational view of the nozzle tip shown in FIG. 45.

FIG. 47 is a distal end view of the nozzle tip shown in FIG. 45.

FIG. 48 is a perspective view of a fourteenth embodiment of a deformable nozzle tip according to the present invention.

FIG. 49 is a side elevational view of the nozzle tip shown in FIG. 48.

FIG. 50 is a distal end view of the nozzle tip shown in FIG. 48.

FIG. 51 is a perspective view of a fifteenth embodiment of a deformable nozzle tip according to the present invention.

FIG. 52 is a side elevational view of the nozzle tip shown in FIG. 51.

FIG. 53 is a distal end view of the nozzle tip shown in FIG. 51.

FIG. 54 is a perspective view of a sixteenth embodiment of a deformable nozzle tip according to the present invention.

FIG. 55 is an end view of the nozzle tip shown in FIG. 54.

FIG. 56 is a distal end view of the nozzle tip shown in FIG. 54 in a substantially deformed configuration.

FIG. 57 is a distal end view of an alternative embodiment the wall portion of the nozzle tip shown in FIG. 54.

FIG. 58 is a distal view of an alternative embodiment of the wall portion of the nozzle tip shown in FIG. 54.

FIG. 59 is a side elevational view of a seventeenth embodiment of a deformable nozzle tip according to the present invention.

FIG. 60 is a side elevational view of the deformable nozzle tip shown in FIG. 59 in a substantially deformed configuration.

FIG. 61 is a distal end view of an eighteenth embodiment of a deformable nozzle portion according to the present invention.

FIG. 62 is a distal end view of the deformable nozzle tip shown in FIG. 61 in a substantially deformed configuration.

FIG. 63 is a distal end view of an alternative embodiment of the deformable nozzle tip shown in FIG. 61.

FIG. 64 is a distal end view of the deformable nozzle portion shown in FIG. 63 in a substantially deformed configuration.

FIG. 65 is a distal end view of a nineteenth embodiment of a deformable nozzle portion according to the present invention.

FIG. 66 is a distal end view of the deformable nozzle portion shown in FIG. 65 in a substantially expanded configuration.

FIG. 67 is a distal end view of the nozzle portion shown in FIG. 65 in a substantially non-deformed configuration.

FIG. 79 is a perspective view of a twenty-third embodiment of a deformable nozzle tip according to the present invention.

FIG. 80 is a side elevational view of the nozzle tip shown in FIG. 79.

FIG. 81 is a distal end view of the nozzle tip shown in FIG. 79.

FIG. 82 is a side elevational view of the nozzle tip shown in FIG. 79 in a substantially deformed configuration.

FIG. 83 is a perspective view of a twenty-fourth embodiment of a deformable nozzle tip according to the present invention.

FIG. 84 is a distal end view of the deformable nozzle tip shown in FIG. 83.

FIG. 85 is a perspective view of a twenty-fifth embodiment of a deformable nozzle tip according to the present invention.

FIG. 86 is a distal end view of the deformable nozzle tip shown in FIG. 85.

FIG. 87 is a perspective view of a twenty-sixth embodiment of a deformable nozzle tip according to the present invention.

FIG. 88 is a distal end view of the deformable nozzle tip shown in FIG. 87.

FIG. 89 is a perspective view of a twenty-seventh embodiment of a deformable nozzle tip according to the present invention.

FIG. 90 is a distal end view of the deformable nozzle tip shown in FIG. 89.

FIG. 91 is a side elevational view of the deformable nozzle portion shown in FIG. 90 in a substantially deformed configuration.

FIG. 92 is a perspective view of a twenty-eighth embodiment of a deformable nozzle tip according to the present invention.

FIG. 93 is a distal end view of the nozzle tip shown in FIG. 92 in a substantially compressed configuration.

FIG. 94 is a distal end view of the nozzle tip shown in FIG. 93.

FIG. 95 is a distal end view of the nozzle tip shown in FIG. 94 in a partially deformed configuration.

FIG. 96 is a distal end view of the nozzle tip shown in FIG. 92 in a substantially deformed configuration.

FIG. 97 is a perspective view of an alternative embodiment of the deformable nozzle tip shown in FIG. 92.

FIG. 98 is a distal end view of the nozzle tip shown in FIG. 97.

FIG. 99 is a distal end view of the nozzle tip shown in FIG. 97 in a partially deformed configuration.

FIG. 100 is a distal end view of the nozzle tip shown in FIG. 97 in a substantially deformed configuration.

FIG. 101 is a distal end view of a twenty-ninth embodiment of a deformable nozzle tip according to the present invention.

FIG. 102 is a distal end view of the deformable nozzle tip shown in FIG. 99 in a partially deformed configuration.

FIG. 103 is a distal end view of the deformed nozzle tip shown in FIG. 99 is a substantially deformed configuration.

DESCRIPTION OF THE PREFERRED EMBODIMENTS

Figure 10:
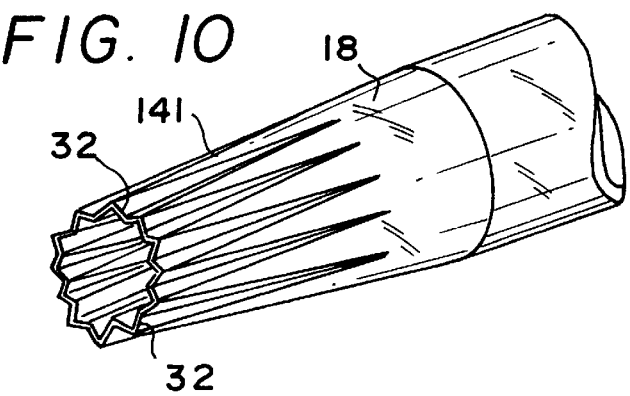
FIG. 10 is a perspective view of a second embodiment of a deformable nozzle tip according to the present invention.
Figure 11:
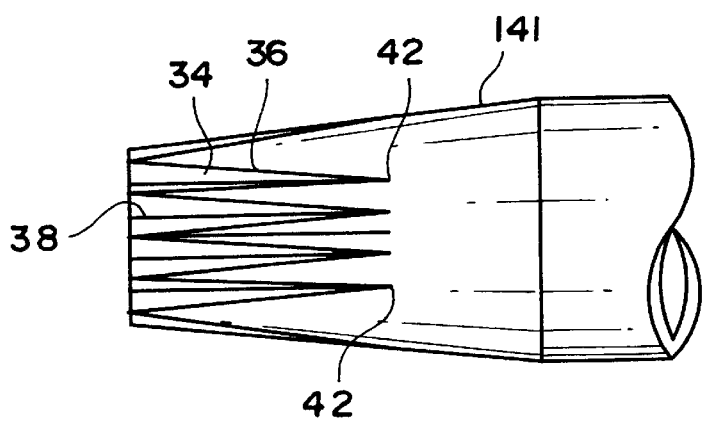
FIG. 11 is a side elevational view of the deformable nozzle tip shown in FIG. 9.
Figure 12:
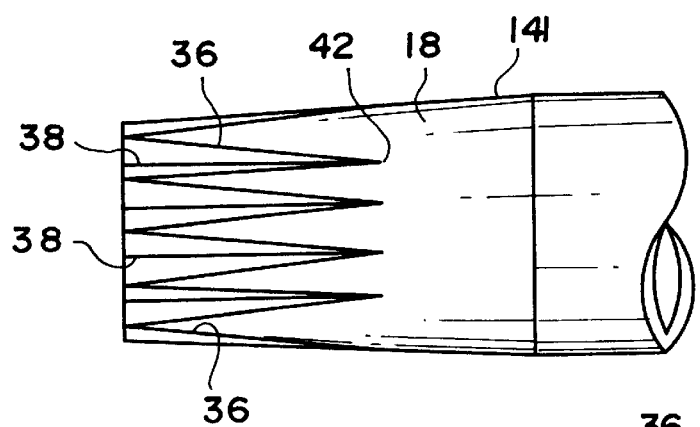
FIG. 12 is a side elevational view of the deformable nozzle tip shown in FIG. 9 in a substantially deformed configuration.

The present invention is directed to devices for implanting a deformable intraocular lens structure within the eye.

A preferred embodiment of a deformable intraocular lens implantation device 210 according to the present invention is shown in FIGS. 1 and 2. The implantation device comprises a microcartridge 212 disposed within a holder 213 comprising a holder body 214 with a receiver 215, and a moveable plunger 216.

Moveable plunger 216 is fitted with an end cap 218 at a proximal end, and fitted with a plunger tip 220 at a distal end. The end cap 218 is provided with a concave end face 222 to allow a person to securely engage end cap 218 with his or her finger tip or tips. The plunger 216 is installed within the holder 213 in a manner to allow the plunger to be reciprocated therein. In the illustrated embodiment, the plunger 216 is supported for sliding movement within the holder 213 by guide 226.

As shown in FIG. 2, microcartridge 212 includes a lens receiving portion 224, an extending portion 228, a nozzle portion 16 and a deformable nozzle tip 14. Lens receiving portion 224 and nozzle portion 16 of microcartridge 212 define a lens delivery passageway portion 230 which communicates with a nozzle tip lens delivery passageway portion 22 through deformable nozzle tip portion 14. Plunger tip 220 is configured to advance a deformable intraocular lens (not shown) through lens delivery passageway portion 230 and nozzle tip lens delivery passageway portion 22.

In use, a deformable intraocular lens is loaded into the proximal end of lens receiving portion 224 of microcartridge 212 which is pre-lubricated with a surgically compatible lubricant. Moveable plunger 216 is moved into a retracted proximal position and microcartridge 212 is loaded into receiver 215. As shown in FIGS. 1 and 2, receiver 215 is configured to engage extending portion 228 and thereby prevent rotational and axial distal movement of the loaded microcartridge 212.

Moveable plunger 216 is then moved distally relative to the holder 213 until plunger tip 220 contacts the loaded deformable intraocular lens. Deformable nozzle tip 14 and a portion of nozzle portion 16 of microcartridge 212 are then placed at and guided through an ocular incision. The moveable plunger 216 is then further moved distally relative to the holder 213 to advance plunger tip 220 and thus, the deformable intraocular lens, through lens delivery passageway portion 230 and nozzle tip lens delivery passageway portion 22 into the eye. Plunger tip 220 may be used to position the intraocular lens within the eye.

An alternative embodiment of a deformable intraocular lens implantation device 210' according to the present invention is shown in FIG. 3. The implantation device 210' comprises a holder 213' including a holder body 214' and an integrated cartridge portion 232', and a moveable plunger 216'.

Moveable plunger 216' is fitted with an end cap 218' at one end, and fitted with a plunger tip 220' at an opposite end. The end cap 218' is provided with a concave end face 222' to allow a person to securely engage end cap 218' with his or her finger tip or tips. The plunger 216' is installed within the holder 213' in a manner to allow the plunger to be reciprocated therein. In the illustrated embodiment, the plunger 216' is supported for sliding movement within the holder 213' by guide 226'.

Integrated cartridge portion 232' comprises a lens receiving port 234', a nozzle portion 16' and a deformable nozzle tip portion 14'. Integrated cartridge portion 232' also defines a lens delivery passageway portion 230' which communicates proximally with lens receiving port 234' and distally with nozzle tip lens delivery passageway portion 22' through deformable nozzle tip portion 14'. Plunger tip 220' is configured to engage a deformable intraocular lens (not shown) in lens receiving port 234' and advance the lens through lens delivery passageway portion 230' and nozzle tip lens delivery passageway portion 22'.

In use, moveable plunger 216' is moved into a retracted proximal position and lens receiving port 234' is lubricated with a surgically compatible lubricant. A deformable intraocular lens is then loaded into lens receiving port 234'. Moveable plunger 216' is then moved distally relative to the holder 213' until plunger tip 220' engages the loaded deformable intraocular lens. Deformable nozzle tip 14' and a portion of nozzle portion 16' of integrated cartridge portion 232' are then placed at and guided through an ocular incision. The moveable plunger 216' is then further moved distally relative to the holder 213' to advance plunger tip 220' and thus, the deformable intraocular lens, through lens delivery passageway portion 230' and nozzle tip lens delivery passageway portion 22' into the eye. Plunger tip 220' may be used to position the intraocular lens within the eye.

Deformable nozzle tip 14 and a partial section of nozzle portion 16 are shown in FIGS. 4–8. Deformable nozzle tip 14 includes a continuous wall portion 18 which extends in a distal direction from the nozzle portion 16 and defines a distally tapering nozzle tip lens delivery passageway portion 22 having an entrance 24 and an exit 26. Nozzle tip lens delivery passageway portion 22 communicates with lens delivery passageway 230 of the deformable intraocular lens implanting device 210. Continuous wall portion 18 may vary in thickness. Alternatively, deformable nozzle tip portion may be defined by a distal portion of nozzle portion 18 having a conical lens delivery passageway portion.

Integral with the wall portion 18 of the deformable nozzle tip 14 shown in FIGS. 4–8 are a pair of diametrically opposed hinges 32. Each hinge 32 includes two (2) substantially planar hinge portions 34. Preferably, hinges 32 are integral with wall portion 18 and may have a reduced wall thickness.

Further, each hinge 32 shown in FIGS. 4–8 defines two (2) base joints 36 and one peak joint 38. The base joints 36 and peak joint 38 of each hinge 32 extend linearly and distally from a convergence point 42 within wall portion 18. As shown in FIG. 7, the width, W, of each hinge portion 34 increases towards the distal end of deformable nozzle tip portion 14. As a consequence and as shown in FIG. 4, each peak joint 38 extends distally towards the longitudinal axis of nozzle tip lens delivery passageway portion 22 at an angle, A, which in the preferred embodiment shown in FIGS. 4–9, is greater than the angle of taper, T, of wall portion 18, shown in FIG. 5.

In operation, the deformable nozzle tip 14 is guided, in the non-deformed configuration shown in FIGS. 4, 5 and 8, through a small incision in the ocular tissue so that the exit 26 of the nozzle tip lens delivery passageway portion 22 is properly oriented in the capsule of the eye. Note that the substantially circular shaped and reduced transverse cross-sectional profile of wall portion 18 at exit 26 provides a deformable nozzle tip portion 14 which is easily placed at an ocular incision. Also note that a nozzle tip according to the present invention may compress as it is guided through an ocular incision as shown in FIG. 7. It is contemplated to provide hinge portions 34 which extend beyond exit 24 and which define a sharp point and/or edges for use in surgically incising the ocular tissue.

Once deformable nozzle tip 14 is properly oriented within the eye, a deformable intraocular lens is advanced into nozzle tip lens delivery passageway portion 22. As the lens is advanced, the lens exerts a radially outwardly directed force against the tapering wall portion 18 of deformable nozzle tip 14. The reactive force against the lens may cause the lens to deform, or, in embodiments of device 102 where the lens is already deformed, to deform further.

As shown in FIGS. 6 and 9, the force of the lens against the wall portion 18 causes the angle between the base joints 36 of each hinge to increase, and consequently, the distance between the peak joint 38 and the plane defined by base In operation, the deformable nozzle tip 14 is guided, in the non-deformed configuration shown in FIGS. 4, 5 and 8, through a small incision in the ocular tissue so that the exit 26 of the nozzle tip lens delivery passageway portion 22 is properly oriented in the capsule of the eye. Note that the substantially circular shaped and reduced transverse cross-sectional profile of wall portion 18 at exit 26 provides a deformable nozzle tip portion 14 which is easily placed at an ocular incision. Also note that a nozzle tip according to the present invention may compress as it is guided through an ocular incision as shown in FIG. 7. It is contemplated to provide hinge portions 34 which extend beyond exit 24 and which define a sharp point and/or edges for use in surgically incising the ocular tissue.

Once deformable nozzle tip 14 is properly oriented within the eye, a deformable intraocular lens is advanced into nozzle tip lens delivery passageway portion 22. As the lens is advanced, the lens exerts a radially outwardly directed force against the tapering wall portion 18 of deformable nozzle tip 14. The reactive force against the lens may cause the lens to deform, or, in embodiments of device 102 where the lens is already deformed, to deform further.

As shown in FIGS. 6 and 9, the force of the lens against the wall portion 18 causes the angle between the base joints 36 of each hinge to increase, and consequently, the distance between the peak joint 38 and the plane defined by base joints 36 of each hinge 32 to decrease. In sum, the force causes an initial deformation of the transverse cross-sectional profile of wall portion 18. Importantly, this initial deformation causes the hinges 32 to become substantially more smooth prior to there being any contact between the advancing lens and hinges 26 thus providing for a deformable lens delivery procedure which is more protective of the integrity of the deformable lens.

In order to reduce the force necessary to deform deformable nozzle tip portion 14, the thickness of the material which defines base joints 36 and peak joints 38 may be decreased. Alternatively, base joints 32 and/or peak joints 38 of deformable nozzle portion 14 may be perforated or otherwise made more flexible.

As the lens is advanced further through the nozzle tip lens delivery passageway portion 22, the lens continues to exert a radially outwardly directed force against wall portion 18. The lens also contacts hinges 32, and in particular, the peak joints 38 thereof. Importantly, the initial deformation of the deformable nozzle tip 14 relaxes the angle at which peak joints 38 extend from convergence points 42 toward the longitudinal axis of nozzle tip lens delivery passageway portion 22. This allows the lens to more easily slide past hinges 32, and in particular, past peak joints 38. To further ease the progression of a deformable intraocular lens through the nozzle tip lens delivery passageway portion 22, peak joints 38 may be rounded.

The force of the lens against the hinges 32 cause the transverse cross-sectional profile of wall portion 18 to deform further. Note by a comparison of FIGS. 8 and 9 that the deformation of wall portion 18 results in an increase in the transverse cross-sectional area of nozzle tip lens delivery passageway portion 22. Specifically, the transverse cross-sectional profile of nozzle tip lens delivery passageway portion becomes elongated as shown in FIG. 9.

The limit of deformation of wall portion 18 is reached when the peak joint 36 of each hinge 32 is substantially coincident with the plane defined by the base joints 34 of the respective hinge 32. Note that for the deformable nozzle tip 14 shown in FIGS. 4–9, the maximum possible transverse cross-sectional area of nozzle tip lens delivery passageway portion 22 occurs at the exit 26 thereof.

Importantly, as the lens is advanced distally towards the exit 26 of nozzle tip lens delivery passageway portion 22, deforming nozzle tip portion 14 allows the lens to return to a non-deformed configuration (i.e. to expand thereby reducing the energy stored therein). The lens may be partially or fully returned from a deformed configuration upon ejection from exit 26. Because the elastic stresses set up in the lens by the deformation procedure are substantially relieved prior to the introduction of the lens into the eye, there is less chance of injury to the eye than if the lens were simply allowed to "spring" back or rapidly return from a deformed configuration to its pre-deformed configuration within the eye. Such "springing" could, for example, damage the capsular bag. There is also less chance of damage occurring to the lens or the lens becoming improperly orientated within the eye. In short, the implantation procedure is improved.

After implantation of the lens in the eye, deformable nozzle tip 14 substantially returns to the non-deformed configuration shown in FIGS. 4, 5 and 8. The deformable nozzle tip 14 may be compressed, as shown in FIG. 7, during withdrawal by surrounding tissue or may be compressed by the transmission of a compressive force on the nozzle portion 16 as, for example, by forceps or the hand of a surgeon at nozzle portion 16 for easily withdrawal from the eye. Hinges 32 may be configured to bias deformable nozzle tip 14 towards a non-deformed configuration. For example, hinge portions 34 may be either convex or concave.

Deformable nozzle tip 14 may be configured to temporarily remain in the deformed configuration shown in FIGS. 6 and 9 after ejection of the lens therefrom. By configuring nozzle tip 14 to temporarily remain in a substantially deformed configuration after lens ejection, the nozzle tip 14 is prevented from exerting a distally oriented force on the intraocular lens. In other words, the deformable nozzle tip 14 is prevented from "squirting" the lens into the eye. For example, deformable nozzle tip portion 14 may be constructed of materials which resume a pre-deformed shape slowly, for example, materials having prescribed memory characteristics. Alternatively, deformable nozzle tip portion 14 may be configured to return to a non-deformed configuration by the force of surrounding tissue against wall portion 18 as the nozzle tip 14 is removed from the eye.

Figure 13:
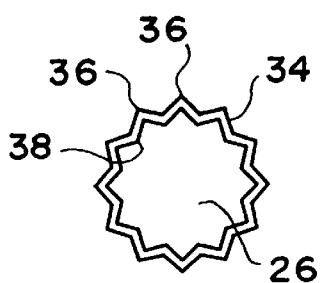
FIG. 13 is a distal end view of the deformable nozzle tip shown in FIG. 11.
Figure 14:
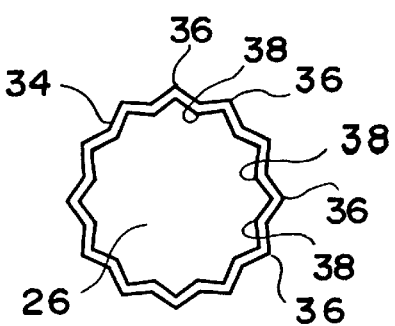
FIG. 14 is a distal end view of the deformable nozzle tip shown in FIG. 12.

A second embodiment of a deformable nozzle tip portion 141 is shown in FIGS. 10–14. Wall portion 18 of deformable nozzle tip 141 includes hinges 32 along the entire perimeter thereof. As shown in FIGS. 13–14, the transverse cross-sectional profile of wall portion 18 tends to deform uniformly about the longitudinal axis of the nozzle tip lens delivery passageway portion 22 as the lens advances through the nozzle tip portion lens delivery passageway 22.

Figure 15:
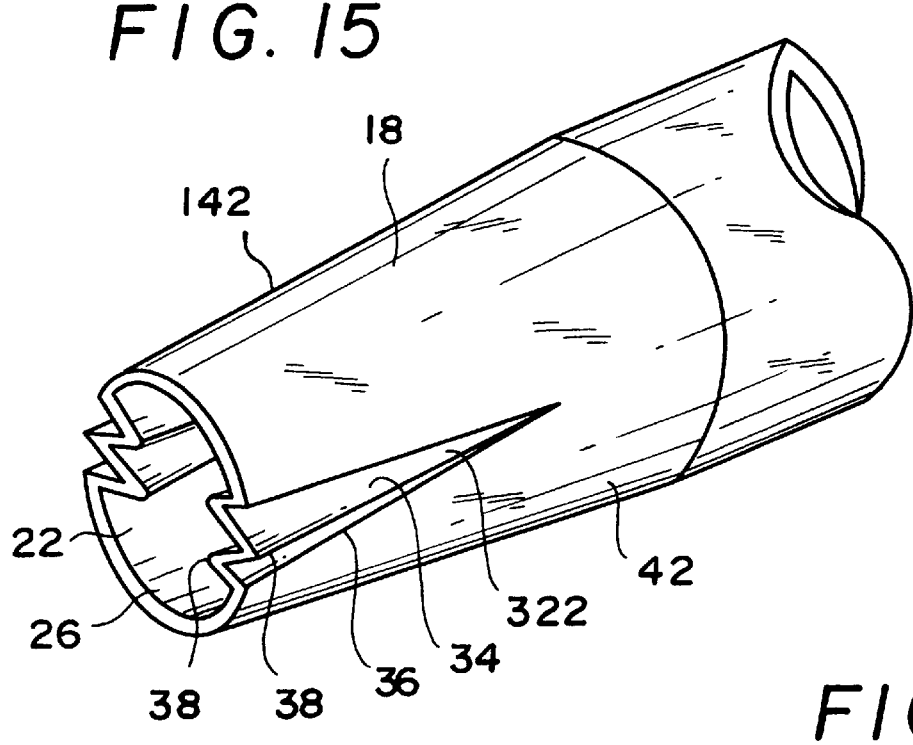
FIG. 15 is a perspective view of a third embodiment of a deformable nozzle tip according to the present invention.
Figure 16:
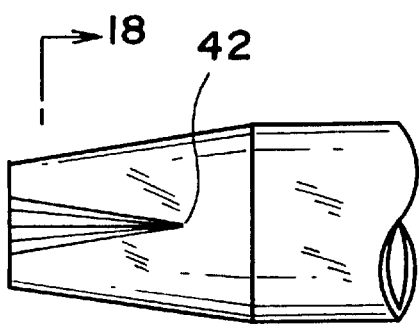
FIG. 16 is a side elevational view of the deformable nozzle tip shown in FIG. 15.
Figure 17:
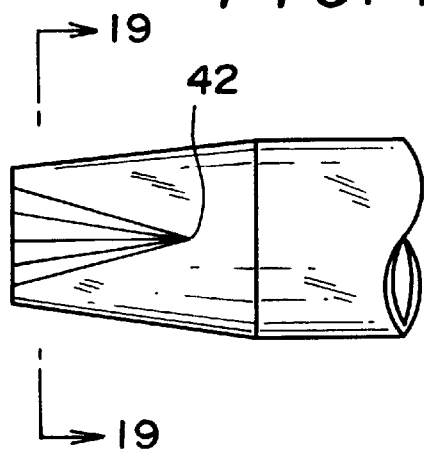
FIG. 17 is a side elevational view of the deformable nozzle tip shown in FIG. 16 in a substantially deformed configuration.
Figure 18:
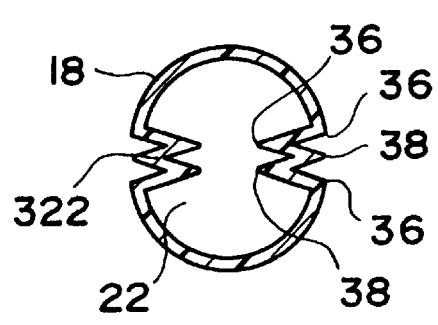
FIG. 18 is a cross-sectional view of the deformable nozzle tip shown in FIG. 16 along the line 18—18.
Figure 19:
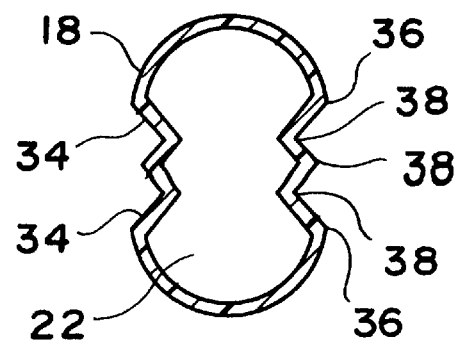
FIG. 19 is a cross-sectional view of the deformable nozzle tip shown in FIG. 17 in a substantially deformed configuration along the line 19—19.
Figure 20:
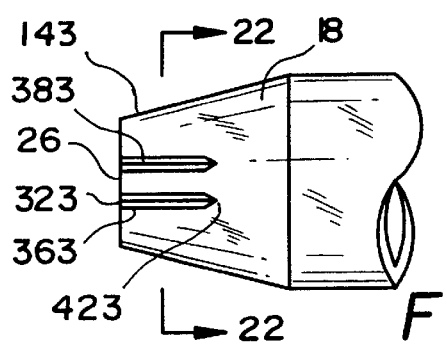
FIG. 20 is a side elevational view of a fourth embodiment of a deformable nozzle tip according to the present invention.
Figure 21:
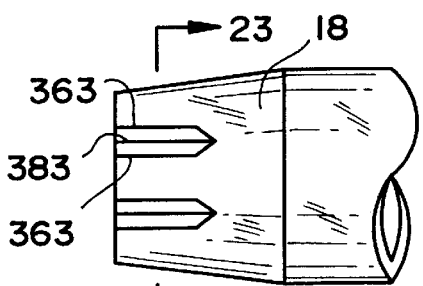
FIG. 21 is a side elevational view of the deformable nozzle tip shown in FIG. 19 in a substantially deformed configuration.
Figure 22:
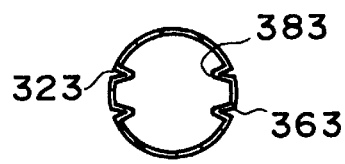
FIG. 22 is a cross-sectional view of the deformable nozzle tip shown in FIG. 20 along the line 22—22.
Figure 23:
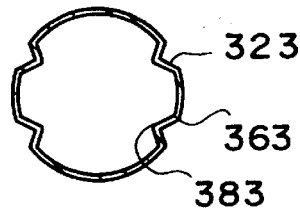
FIG. 23 is a cross-sectional view of the deformable nozzle tip shown in FIG. 21 in a substantially deformed configuration along the line 23—23.

A third embodiment of a deformable nozzle tip portion 142 is shown in FIGS. 15–19. Wall portion 18 of deformable nozzle tip 142 includes a pair of diametrically opposed hinges 322. As shown in FIG. 15, each hinge 322 is made of four (4) hinge portions 34 which define three (3) peak joints 38 and two base joints 36. Peak joints 38 and base joints 36 of each binge 322 extend from a common point 42 within wall portion 18 of deformable nozzle tip portion 141. Note from a comparison of FIGS. 9 and 19 that by increasing the number of hinge portions within hinge 32(322), the extent to which the transverse cross-sectional profile of wall portion 18 elongates is also increased.

A fourth embodiment of a deformable nozzle tip portion 143 is shown in FIGS. 20–23. Wall portion 18 includes four hinges 323. Curvilinear base joints 363 and linear peak joint 383 of each hinge 323 extend from convergence point 42 within wall portion 18. The distal portions of base joints 363 of each hinge 323 are substantially parallel.

Figure 24:
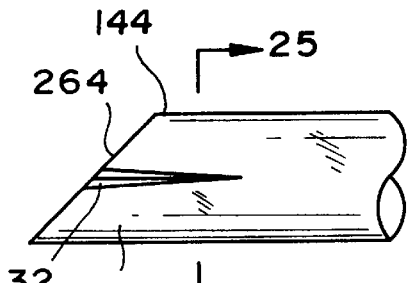
FIG. 24 is a side elevational view of a fifth embodiment of a deformable nozzle tip according to the present invention.
Figure 25:
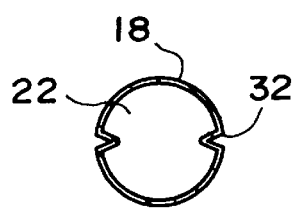
FIG. 25 is a cross-sectional view of the deformable nozzle tip shown in FIG. 24 along the line 25—25.
Figure 26:
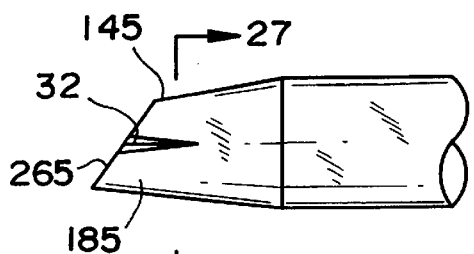
FIG. 26 is a side elevational view of a sixth embodiment of a deformable nozzle tip according to the present invention.
Figure 27:
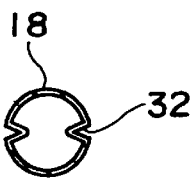
FIG. 27 is cross-sectional view of the deformable nozzle tip shown in FIG. 25 along the line 26—26.

A fifth embodiment of a deformable nozzle tip portion 144 is shown in FIGS. 24 and 25. As shown in FIG. 24, hinges 32 may be included in a wall portion 184 which does not taper. As is further shown in FIG. 24, hinges 32 may also be included in a wall portion 184 having an exit 264 which defines a plane, the normal of which is not coincident with, but rather, defines an angle relative to, the longitudinal axis of the nozzle tip lens delivery passageway 22. As shown in the sixth embodiment of deformable nozzle tip portion 145 in FIGS. 26 and 27, hinges 32 may also be included in a wall portion 185 which tapers and which has an exit 265 which defines a plane, the normal of which is at an angle relative to the longitudinal axis of the nozzle tip lens delivery passageway portion 22.

Figure 28:
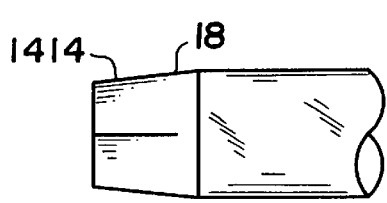
FIG. 28 is a side elevational view of a seventh embodiment of a deformable nozzle tip according to the present invention.
Figure 29:
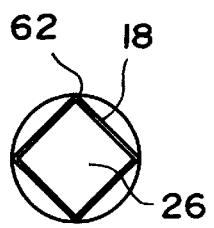
FIG. 29 is an end view of the nozzle tip shown in FIG. 28.
Figure 30:
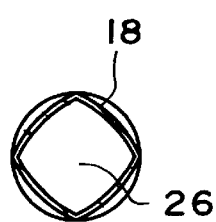
FIG. 30 is an end view of the nozzle tip shown in FIG. 28 in a substantially deformed configuration.
Figure 68:
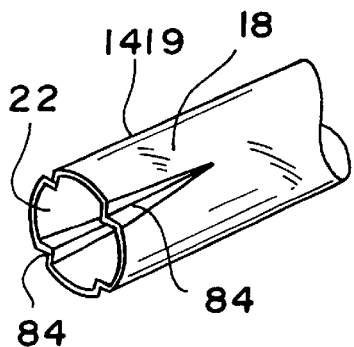
FIG. 68 is a perspective view of a twentieth embodiment of a deformable nozzle tip according to the present invention.
Figure 69:
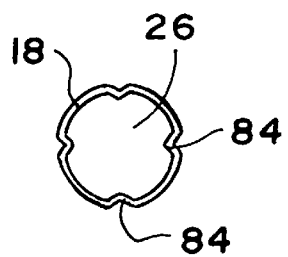
FIG. 69 is a distal end view of the deformable nozzle tip shown in FIG. 68.
Figure 70:
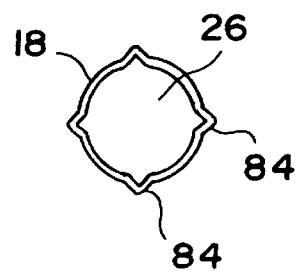
FIG. 70 is a distal end view of the deformable nozzle tip shown in FIG. 69 in a substantially deformed configuration.

A seventh embodiment of a deformable nozzle tip portion 1414 is shown in FIGS. 28–30. The transverse cross-sectional profile of wall portion 18 is substantially square shaped and defines a tapering nozzle tip lens delivery passageway portion 22. Note from FIGS. 28–30 that corners 62 remain stationary during deformation of the transverse cross-sectional profile of wall portion 18.

An eighth embodiment of a deformable nozzle tip portion 146 is shown in FIGS. 31–35. As shown in FIGS. 31, 33, and 35, wall portion 18 of nozzle tip portion 146 includes a pair of diametrically opposed expansion zones 46. Preferably, and as shown in FIGS. 31–35, expansion zones 46 are substantially triangular shaped regions of reduced wall thickness within wall portion 18. Expansion zones 46 are preferably configured to undergo elastic and/or plastic deformation as a deformable lens is advanced through the nozzle tip lens delivery passageway portion 22 thereby allowing for the transverse cross-sectional profile of wall portion 18 to deform.

A ninth embodiment of a deformable nozzle tip portion 147 including a pair of diametrically opposed expansion zones 461 is shown in FIGS. 36–41. As shown in FIGS. 36–41, expansion zones 461 are regions of reduced wall thickness within wall portion 18 which are configured to fail, preferably by tearing at a predetermined location 48 within each expansion zone 461, as a lens is advanced through nozzle tip lens delivery passageway portion 22. Expansion zones 461 may be configured to undergo elastic and/or plastic deformation prior to failing.

A tenth embodiment of a non-tapering deformable nozzle tip portion 148 including a pair of substantially rectangular shaped expansion zones 462 is shown in FIGS. 36–38. In the eleventh embodiment of a deformable nozzle tip portion 149 shown in FIG. 41, an expansion zone 463 is coextensive with a slot 48 in wall portion 18. The slot 48 shown in FIGS. 41–42 extends from the exit 26 of nozzle tip lens delivery passageway 22 to the curved distal edge of expansion zone 463. A twelfth embodiment of a deformable nozzle tip portion 1410 shown in FIGS. 43–44 includes independent slots 481 and expansion zones 464 in wall portion 18.

In alternative contemplated embodiments of a deformable nozzle tip portion, expansion zones 46 may be regions within wall portion 18 which have been weakened chemically, for example, etched, or mechanically, for example, pre-stretched. Further, expansion zones 46 may have the same wall thickness as the rest of wall portion 18.

A thirteenth embodiment of a deformable nozzle tip portion 1411 is shown in FIGS. 45–47. Wall portion 18 defines a contiguous flap 54 and an optional longitudinal groove 52. As a deformable lens is advanced through nozzle tip lens delivery passageway 22, a portion of the lens engages groove 52 which guides the deformable intraocular lens into contact with flap 54. The advancing lens causes flap 52 to pivot resulting in a deformation of the transverse cross-sectional profile of wall portion 18. Note that flap 52 dampens the return of the lens to a non-deformed configuration as the lens advances through angled exit 26 of the nozzle tip lens delivery passageway portion 22. The lens is thereby prevented from "springing" out of deformable nozzle tip portion 1411.

A fourteenth embodiment of a deformable nozzle tip portion 1412 is shown in FIGS. 48–50. Wall portion 18 of nozzle tip portion 1412 defines distally extending flexible petals 76. Note that the substantially hemispherical shaped nozzle tip portion 1412 provides a substantially closed exit 26 which is more easily placed at and guided through an ocular incision. When contacted by an advancing deformable intraocular lens, flexible petals open outwardly resulting in a deformation of the transverse cross sectional profile of wall portion 18.

A fifteenth embodiment of a deformable nozzle tip portion 1413 is shown in FIGS. 51–53. Wall portion 18 includes semi-rigid fingers 58 which extend longitudinally along the corners 62 of the nozzle tip lens delivery passageway portion 22. When a deformable intraocular lens is advanced through nozzle tip lens delivery passageway portion 22, the transverse cross-sectional profile of wall portion 18 deforms. Semi-rigid fingers 58 prevent nozzle tip lens delivery passageway portion 22 of deformable nozzle tip 1413 from excessively deflecting from the longitudinal axis of the nozzle lens delivery passageway 102 of nozzle portion 16.

A sixteenth embodiment of a deformable nozzle tip portion 1415 is shown in FIGS. 54–56. Wall portion 18 defines a proximal tapering nozzle tip lens delivery passageway portion 2211 and a distal nozzle tip lens delivery passageway portion 2212. The transverse cross-sectional profile of wall portion 18 along proximal tapering nozzle tip lens delivery passageway portion 2211 is rigid and non-deforming. The substantially rectangular shaped transverse cross-sectional profile of wall portion 18 along distal nozzle tip lens delivery passageway portion 2212 deforms as shown in FIG. 56.

The thickness of wall portion 18 along proximal nozzle tip lens delivery passageway portion 2212 may be varied to alter the manner in which the transverse cross-sectional profile of wall portion 18 along proximal nozzle tip lens delivery passageway portion 2212 deforms. For example, the short sides of the substantially rectangular shaped transverse cross-sectional profile of wall portion 18' along the distal nozzle tip lens delivery passageway portion 2212 shown in FIG. 57 are thicker than the long sides thereof. Alternatively, the long sides of the substantially rectangular shaped transverse cross-sectional profile of wall portion 18" along the distal nozzle tip lens delivery passageway portion 2212 shown in FIG. 59 are thicker than the short sides thereof.

A seventeenth embodiment of a deformable nozzle tip portion 1416 is shown in FIGS. 59–60. The transverse cross-sectional profile of wall portion 18 is substantially tubular and elastic. As shown in FIG. 59, the transverse cross-sectional profile of wall portion 18 conforms to the profile of the advancing intraocular lens.

An eighteenth embodiment of a deformable nozzle tip portion 1417 is shown in FIGS. 61–62. The substantially crescent shaped transverse cross-sectional profile of wall portion 18 defines a first arcuate portion 64 having a greater radius of curvature than a second arcuate portion 66 thereof. As a deformable intraocular lens is advanced through nozzle tip lens delivery passageway portion 22, the transverse cross-sectional profile of wall portion 18 deforms as shown in FIG. 62. It is important to recognize that both first and second arcuate portions 64 and 66 bias against the radially outward deformation of second arcuate portion 66. Slots 72 in deformable nozzle tip 1417' shown in FIGS. 63 and 64 decrease the force necessary to deform second arcuate portion 66.

A nineteenth embodiment of a deformable nozzle tip portion 1418 is shown in FIGS. 65–67. The transverse cross-sectional profile of wall portion 18 defines an arcuate portion 74, a first arm portion 76 and a second arm portion 78. Preferably, first and second arm portions 76,78 are of an equal length which is greater than the radius of curvature of arcuate portion 74. However, first and second arm portions 76,78 may have different lengths as long as the combined total length of first and second arm portions 76,78 is greater than double the radius of curvature of arcuate portion 74.

As a lens is advanced through the nozzle tip lens delivery passageway portion 22 of deformable nozzle tip portion 1418, first and second arm portions 76,78 deflect away from arcuate portion 74. The deflection of arms 76,78 causes a stress to be induced in arcuate portion 74. The stress in arcuate portion 74 biases arms 76,78 to the configuration shown in FIG. 64. The stress in arcuate portion 74 reaches a maximum when deflecting arms 76,78 define a straight line path between the ends of arcuate portion 74. As arms 76,78 further deflect away from arcuate portion 74, the stress induced in arcuate portion 74 biases arms 76,78 into the configuration shown in FIG. 66. It is important to recognize that the force of deformable wall portion 18 against an advancing lens is substantially released when the transverse cross-sectional profile of wall portion 18 deforms to the configuration shown in FIG. 66. Nozzle tip portion 1418 returns to the non-expanded configuration shown in FIG. 67 by the force of tissue against wall portion 18 during removal of the nozzle tip portion 1418 from the eye.

Figure 71:
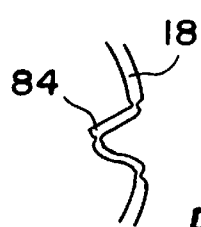
FIG. 71 is a partial distal end view of the deformable nozzle tip shown in FIG. 68.
Figure 72:
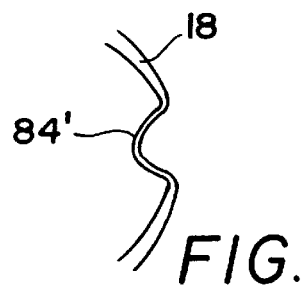
FIG. 72 is a partial distal end view of an alternative embodiment of the deformable nozzle tip shown in FIG. 68.

A twentieth embodiment of a deformable nozzle tip 1419 is shown in FIGS. 68–72. Wall portion 18 includes four (4) expansion assemblies 84. Expansion assemblies 84 are sections of wall portion 18 which deflect without creating substantial stress in adjacent sections of wall portion 18. The transverse cross sectional profile of wall portion 18 deforms as shown in FIGS. 71–72. As shown in FIG. 71, each expansion assembly 84 is preferably a section of wall portion 18 which has been rendered substantially weak by, for example, the removal of material therefrom. As another example, an expansion assembly 84', shown in FIG. 72, may be created in wall portion 18 by continuous plastic deformation of a section of wall portion 18.

Figure 73:
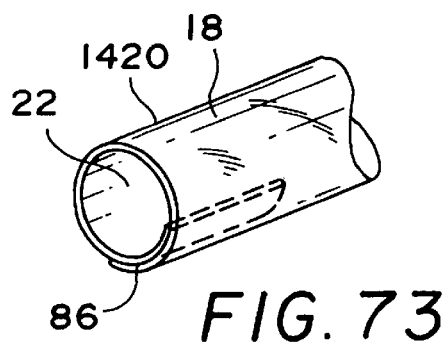
FIG. 73 is a perspective view of a twenty-first embodiment of a nozzle tip according to the present invention.
Figure 74:
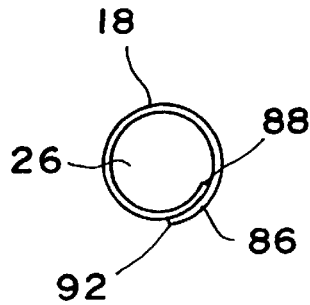
FIG. 74 is a distal end view of the deformable nozzle tip shown in FIG. 73.
Figure 75:
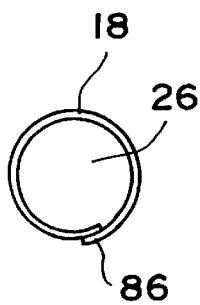
FIG. 75 is a distal end view of the deformable nozzle tip shown in FIG. 73 in a substantially deformed configuration.

A twenty-first embodiment of a deformable nozzle tip 1420 is shown in FIGS. 73–75. Wall portion 18 includes an overlap portion 86. When a lens is advanced through nozzle tip lens delivery passageway 22, the force of the lens against wall portion 18 causes the inner surface of overlap portion 86 of wall portion 18 to slide over the adjacent outer surface of wall portion 18. As shown in FIGS. 74–75, the transverse cross-sectional profile of wall portion 18 is thereby deformed. To prevent the edge 88 of overlap portion 86 from sliding past edge 92 of wall portion 18, a barb and catch assembly (not shown) may be included therebetween.

Figure 76:
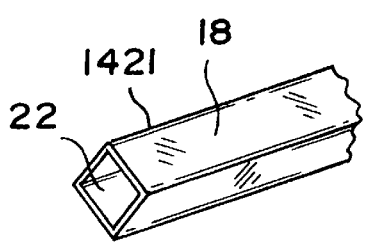
FIG. 76 is a perspective view of a twenty-second embodiment of a deformable nozzle tip according to the present invention.
Figure 77:
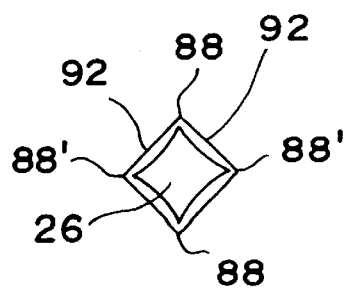
FIG. 77 is a distal end view of the of the deformable nozzle tip shown in FIG. 75.
Figure 78:
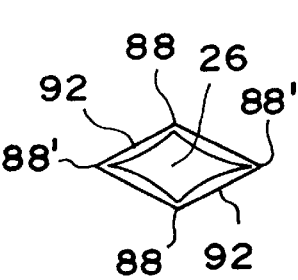
FIG. 78 is a distal end view of the of the deformable nozzle tip shown in FIG. 76 in a substantially deformed configuration.

A twenty-second embodiment of a deformable nozzle tip 1421 is shown in FIGS. 76–78. As shown in FIG. 76, the transverse cross-sectional profile of wall portion 18 is substantially square shaped. Further, the thickness of wall portion 18 at corners 88 and 88' is substantially less than along the sides 92 thereof. As a lens is advanced through nozzle tip 1421, sides 92 are forced to pivot about corners 88 and 88'. For example, as shown in FIG. 78, corners 88' are forced farther apart and corners 88 are forced closer together. The increased dimension of the transverse cross-sectional profile of wall portion 18 defined by the distance between corners 88' allows the deformed intraocular lens to release a portion of the stress associated with lens deformation.

A twenty-third embodiment of a deformable nozzle tip 1422 is shown in FIGS. 79–81. Wall portion 18 includes a first jaw 94, a second jaw 96, and diametrically opposed slots 98. As a lens is advanced through nozzle tip lens delivery passageway portion 22, first and second jaws 96 and 98, respectively, pivot and thereby cause the transverse cross-sectional profile of wall portion 18 to deform. Importantly, slots 98 are of sufficient size to prevent nozzle portion 16 from collapsing or otherwise deforming during pivoting of first and second jaw portions 96 and 98, respectively.

A twenty-fourth embodiment of a deformable nozzle tip 1423 is shown in FIGS. 83–84. As shown in FIG. 84, the transverse cross-sectional profile of wall portion 18 defines a first arcuate portion 102 having a slot 106 and a second arcuate portion 104.

A twenty-fifth embodiment of a deformable nozzle tip 1424 is shown in FIGS. 85–86. As shown in FIG. 86, the transverse cross-sectional profile of wall portion 18 defines a first arcuate portion 102' having a slot 106' and a second arcuate portion 104' having a slot 106".

A twenty-sixth embodiment of a deformable nozzle tip 1425 is shown in FIGS. 87–88. As shown in FIG. 86, the transverse cross-sectional profile of wall portion 18 defines an outer portion including a first arcuate portion 108 and a second arcuate portion 112. First and second arcuate portions 108 and 112, respectively, are separated by opposed outer portion slots 114. The transverse cross-sectional profile of wall portion 18 also defines an inner portion including a first jaw portion 116 and a second jaw portion 118. First and second jaw portions 116 and 118, respectively, are separated by opposed inner portion slots 122. Importantly, inner portion slots 122 are in perpendicular relation to outer portion slots 114. The arrangement of slots in deformable nozzle tip 1425 prevents an advancing lens from escaping nozzle portion lens delivery passageway 22. Further, note that outer portion arcuate portions 108 and 112, respectively, provide bias against the outward deflection of inner portion jaw portions, 116 and 118, respectively.

A twenty-seventh embodiment of a deformable nozzle tip 1426 is shown in FIGS. 89–91. The transverse cross-sectional profile of wall portion 18 defines a first arcuate portion 124 and a second arcuate portion 126. First and second arcuate portions 124 and 126, respectively, are separated by opposing slots 128. As shown in FIG. 91, wall portion 18 also includes a pair of opposing longitudinal plunger tip engaging ramp portions 132. Note that ramp portions 132 terminate substantially proximally of exit 26 of nozzle tip lens delivery passageway portion 22. As shown in FIG. 91, as plunger tip 202 and a deformable intraocular lens (not shown) are advanced through nozzle tip lens delivery portion 22, plunger tip 202 engages ramps 132 and thereby outwardly deflects first and second arcuate portions 124 and 126, respectively. It is important to recognize that plunger tip 202 deforms the transverse cross-sectional profile of wall portion 18. Also, note that plunger tip 202 engages ramps 132 before the deformable lens (not shown) passes through exit 26 of nozzle tip lens delivery passageway portion 22. Thus, stresses in the lens associated with deformation are substantially relieved from the lens prior to the lens entering the eye.

In an alternative embodiment (not shown), longitudinal channels terminating proximally of the exit 26 of nozzle tip lens delivery passageway 22 may be provided in wall portion 18. A plunger tip including radial protrusions for engaging the channels in wall portion 18 may be provided. As the plunger tip advances past the termination point of the channels in wall portion 18, the plunger tip protrusions will cause the transverse cross-sectional profile of wall portion 18 to deform.

A twenty-eighth embodiment of a deformable nozzle tip 1427 is shown in FIGS. 92–96. As shown in FIG. 92, the transverse cross sectional profile of wall portion 18 preferably defines a set of four (4) spoke portions, each including a bias corner portion 134 and side portions 136. Note the compressibility of deformable nozzle tip 1427 in FIG. 93. As shown in FIG. 95, the wall thickness of wall portion 18 between side portions 136 of adjacent spoke portions is preferably a reduced thickness portion 138 for reducing the amount of force necessary to deform the transverse cross-sectional profile of wall portion 18. However, as shown in the alternative embodiment of expandable nozzle tip 1427' in FIG. 97, it is not necessary to include reduced thickness portions 136 within the transverse cross-sectional profile of wall portion 18. As shown in FIG. 98, bias corner portions 134 bias the transverse cross-sectional profile of wall portion 18 towards the substantially closed configuration shown in FIG. 94.

A twenty-ninth embodiment of a deformable nozzle tip 1428 is shown in FIGS. 101–103. The transverse cross-sectional profile of wall portion 18 includes pleats 142. As a lens is advanced through nozzle tip lens delivery passageway 22 and exit 26 thereof, the transverse cross-sectional profile of wall portion 18 deforms as shown in FIGS. 103–104. Pleats 142 bias the transverse cross-sectional profile of wall portion 18 to the non-deformed configuration shown in FIG. 102.

What is claimed is:

1. A deformable intraocular lens implanting device for implanting a deformable intraocular lens into the eye, said device comprising:
   a holder having a receiver;
   a plunger movably disposed relative to said holder, said plunger having a plunger tip;
   a microcartridge disposed within said receiver, said microcartridge including a lens receiving portion;
   a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;
   wherein said wall portion includes at least one hinge having at least two hinge portions which define at least two base joints and at least one peak joint and wherein said at least two base joints and said at least one peak joint extend distally from a convergence point in said wall portion.

2. A device according to claim 1 wherein the width of said at least two hinge portions increases distally.

3. A device according to claim 1, wherein said wall portion of said nozzle tip portion defines a proximal nozzle tip lens delivery passageway portion, said wall portion along said proximal nozzle tip lens delivery passageway portion being rigid and non-deformable, and a distal nozzle tip lens delivery passageway portion, said wall portion along said distal nozzle tip lens delivery passageway being deformable.

4. A device according to claim 1, wherein said deformation of said transverse cross-sectional profile of said wall portion is elastic.

5. A deformable intraocular lens implanting device for implanting a deformable intraocular lens into the eye, said device comprising:
   a holder having a receiver;
   a plunger movably disposed relative to said holder, said plunger having a plunger tip;
   a microcartridge disposed within said receiver, said microcartridge including a lens receiving portion;
   a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;
   wherein said wall portion of said nozzle tip portion includes at least one semi-rigid finger extending longitudinally along the nozzle tip lens delivery passageway portion.

6. A deformable intraocular lens implanting device for implanting a deformable intraocular lens into the eye, said device comprising:
   a holder having a receiver;
   a plunger movably disposed relative to said holder, said plunger having a plunger tip;
   a microcartridge disposed within said receiver, said microcartridge including a lens receiving portion;
   a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;
   wherein said wall portion has a transverse cross-sectional profile which defines a first arcuate portion having a greater radius of curvature than a second opposed arcuate portion thereof.

7. A deformable intraocular lens implanting device for implanting a deformable intraocular lens into the eye, said device comprising:
   a holder having a receiver;
   a plunger movably disposed relative to said holder, said plunger having a plunger tip;
   a microcartridge disposed within said receiver, said microcartridge including a lens receiving portion;

a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;

wherein said wall portion has a transverse cross-sectional profile which defines an arcuate portion, a first arm, and a second arm, said first arm having a first length and said second arm having a second length wherein the sum of said first length and said second length is greater than double the radius of curvature of said arcuate portion.

8. A deformable intraocular lens implanting device for implanting a deformable intraocular lens into the eye, said device comprising:

a holder having a receiver;

a plunger movably disposed relative to said holder, said plunger having a plunger tip;

a microcartridge disposed within said receiver, said microcartridge including a lens receiving portion;

a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;

wherein said wall portion has a transverse cross-sectional profile which defines a substantially square shape wherein the wall thickness of said wall portion is thicker along the sides than at the corners thereof.

9. A deformable intraocular lens implanting device for implanting a deformable intraocular lens into the eye, said device comprising:

a holder having a receiver;

a plunger movably disposed relative to said holder, said plunger having a plunger tip;

a microcartridge disposed within said receiver, said microcartridge including a lens receiving portion;

a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;

wherein said transverse cross-sectional profile of said wall portion defines an outer portion including a first arcuate portion and a second arcuate portion, said first and second arcuate portions being separated by opposed outer portion channels and an inner portion including a first jaw portion and a second jaw portion, said first and second jaw portions being separated by opposed inner portion channels, said opposed inner portion channels being in perpendicular relation to said outer portion channels.

10. A deformable intraocular lens implanting device for implanting a deformable intraocular lens into the eye, said device comprising:

a holder having a receiver;

a plunger movably disposed relative to said holder, said plunger having a plunger tip;

a microcartridge disposed within said receiver, said microcartridge including a lens receiving portion;

a nozzle portion connected to said lens receiving portion with a lens delivery passageway extending therethrough, said nozzle portion including a deformable nozzle tip portion having a wall portion defining a nozzle tip lens delivery passageway portion, said wall portion having a deformable transverse cross-sectional profile which deforms as an intraocular lens is advanced through said nozzle tip lens delivery passageway portion;

wherein said transverse cross-sectional profile of said wall portion defines a set of spoke portions wherein each spoke portion includes a bias corner portion and two side portions.

* * * * *